United States Patent
Huter et al.

[11] Patent Number: 6,139,511
[45] Date of Patent: *Oct. 31, 2000

[54] GUIDEWIRE WITH VARIABLE COIL CONFIGURATION

[75] Inventors: Scott J. Huter; William J. Boyle, both of Temecula, Calif.; Richard S. Stack, Chapel Hill, N.C.

[73] Assignee: Advanced Cardiovascular Systems, Inc., Santa Clara, Calif.

[*] Notice: This patent issued on a continued prosecution application filed under 37 CFR 1.53(d), and is subject to the twenty year patent term provisions of 35 U.S.C. 154(a)(2).

[21] Appl. No.: 09/106,918

[22] Filed: Jun. 29, 1998

[51] Int. Cl.⁷ .................................................... A61B 5/00
[52] U.S. Cl. ............................................. 600/585; 604/96
[58] Field of Search ................................. 600/585, 433, 600/434; 604/95, 96, 280, 281

[56] References Cited

U.S. PATENT DOCUMENTS

| | | | |
|---|---|---|---|
| 3,452,742 | 7/1969 | Muller | 128/2 |
| 4,719,924 | 1/1988 | Crittenden et al. | 128/772 |
| 4,721,117 | 1/1988 | Mar et al. | 128/772 |
| 4,724,846 | 2/1988 | Evans, III | 600/585 |
| 4,763,647 | 8/1988 | Gambale | 128/657 |
| 4,922,924 | 5/1990 | Gambale et al. | 600/585 |
| 5,069,217 | 12/1991 | Fleischhackor, Jr. | 600/585 |
| 5,084,022 | 1/1992 | Claude | 604/164 |
| 5,107,852 | 4/1992 | Davidson et al. | 600/585 |
| 5,147,317 | 9/1992 | Shank et al. | 604/164 |
| 5,174,302 | 12/1992 | Palmer | 128/772 |
| 5,228,453 | 7/1993 | Sepetka | 128/772 |
| 5,253,653 | 10/1993 | Daigle et al. | 600/585 |
| 5,267,574 | 12/1993 | Viera et al. | 128/772 |
| 5,330,521 | 7/1994 | Cohen | 607/122 |
| 5,345,945 | 9/1994 | Hodgson et al. | 128/772 |
| 5,353,808 | 10/1994 | Viera | 128/772 |
| 5,365,942 | 11/1994 | Shank | 128/772 |
| 5,368,048 | 11/1994 | Stoy et al. | 128/772 |
| 5,385,578 | 1/1995 | Bush et al. | 607/122 |
| 5,406,960 | 4/1995 | Corso, Jr. | 128/772 |
| 5,409,004 | 4/1995 | Sloan | 128/657 |
| 5,433,200 | 7/1995 | Fleischhacker, Jr. | 128/657 |
| 5,460,187 | 10/1995 | Daigle et al. | 123/772 |
| 5,465,732 | 11/1995 | Abele | 128/772 |

(List continued on next page.)

OTHER PUBLICATIONS

Magic Torque, Ref. 46–592, Package Includes 1 guidewire, 1 torque vise, Lot Number 418849, Expiration date 1999–10, Meditech, Boston Scientific Corporation, 480 Pleasant Street, Watertown, MA 02172 (617) 923–1720/ (800) 225–3238. Instructions for use 801444–02, Rev. 4/94.

*Primary Examiner*—Cary O'Connor
*Assistant Examiner*—Pamela Wingood
*Attorney, Agent, or Firm*—Heller Ehrman White & McAuliffe LLP

[57] ABSTRACT

The present invention is directed to a guidewire having an elongate core member with a proximal section and a distal section. The distal section has at least one tapered segment, wherein the elongate core member tapers distally to a reduced diameter. Preferably, the tapered segments of the distal section of the elongate core member are marked with radiopaque markers to indicate where a tapered segment begins or ends. A proximal coil having a rectangular cross section and at least one distal coil having a round cross section are disposed around at least a portion of the distal section of the elongate core member. The proximal end of the proximal coil is attached to the distal section of the elongate core member. The distal coils can be made of a material that is radiopaque or non-radiopaque. If one of the distal coils is radiopaque, it may be made from a radiopaque material or it may be made of a hollow tube of non-radiopaque material that is filled with material that is at least partially radiopaque. The proximal end of the distal most coil is attached to the distal end of the proximal coil, and the distal end of the distal most coil is attached to the distal section of the elongate core member.

21 Claims, 3 Drawing Sheets

U.S. PATENT DOCUMENTS

| | | | |
|---|---|---|---|
| 5,479,938 | 1/1996 | Weier | 128/772 |
| 5,483,022 | 1/1996 | Mar | 174/128.1 |
| 5,497,783 | 3/1996 | Urick et al. | 128/772 |
| 5,498,250 | 3/1996 | Prather | 604/280 |
| 5,520,194 | 5/1996 | Miyata et al. | 600/585 |
| 5,522,872 | 6/1996 | Hoff | 607/119 |
| 5,606,981 | 3/1997 | Tartacower et al. | 128/772 |
| 5,628,787 | 5/1997 | Mayer | 623/1 |
| 5,630,840 | 5/1997 | Mayer | 623/1 |
| 5,647,127 | 7/1997 | Miyata et al. | 29/896.9 |
| 5,679,470 | 10/1997 | Mayer | 428/662 |
| 5,682,894 | 11/1997 | Orr et al. | 128/654 |
| 5,695,469 | 12/1997 | Segal | 604/104 |

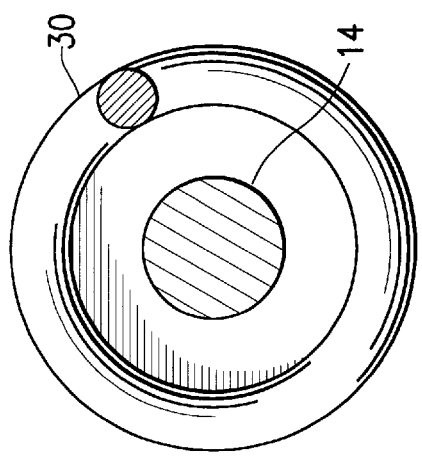
FIG. 4
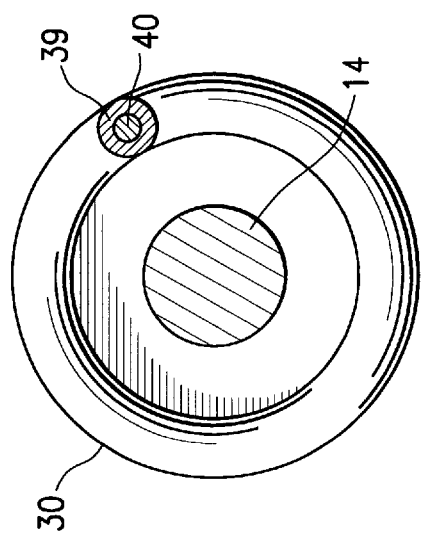
FIG. 6A
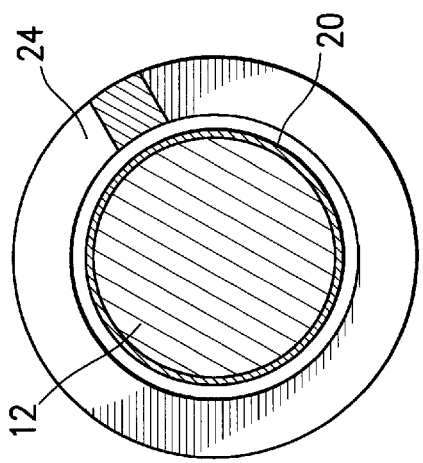
FIG. 6B
FIG. 5

GUIDEWIRE WITH VARIABLE COIL CONFIGURATION

BACKGROUND

This invention relates to the field of guidewires for advancing intraluminal devices such as stent delivery catheters, balloon dilatation catheters, atherectomy catheters and the like within body lumens.

The most common method for insertion of percutaneous catheters is the Seldinger technique. In this procedure, a local anesthesia is delivered and a skin puncture is made proximal to the femoral or brachial artery with an obturator positioned within a cannula. Once inside the artery, the obturator is removed, and the guidewire is inserted through the cannula into the artery. The guidewire is then advanced into the vasculature guided by fluoroscopic imaging to the desired site. Generally, the distal tip of the guidewire is pre-shaped or has the ability to be shaped within the vessel in order to steer the guidewire to the desired location by rotating and advancing in combination. Once the guidewire is in the desired location, a diagnostic or therapeutic catheter is advanced over the guidewire, and the desired procedure is performed.

Further details of guidewires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); and U.S. Pat. No. 5,345,945 (Hodgson, et al.) which are hereby incorporated by reference in their entirety.

Because of the environment that guidewires are used in, and the purpose they serve, it is desirable to have several basic features for most, if not all, guidewires. The guidewire must navigate and advance within the lumens of a patient, coming into contact with delicate tissue. For this reason, the guidewire requires a soft, flexible distal tip which can be manipulated without causing injury to the vessel walls. Also, it must be sufficiently maneuverable to reach the required destination, which requires stable tortional characteristics, and a rigid proximal shaft that can be pushed to advance the guidewire. These characteristics are difficult to achieve, as one tends to negate the other. It is also desirable for the outer diameter of the guidewire fit properly within the inside diameter of the lumen within which it is disposed. This can be problematic for guidewires designed for the peripheral arteries, such as those found within the legs and arms, because the size of the diagnostic and therapeutic devices used in these arteries are typically large, requiring a large outer diameter guidewire, which can be stiff and inflexible due to its size. In addition, because the guidewire is steered to the desired location within the vasculature under fluoroscopy, a radiopaque marker of some type is required, which is typically a precious metal coil, band or solder. Because of the size of the peripheral guidewire, a precious metal coil can be expensive to manufacture.

Conventional guidewires for angioplasty, stent delivery, atherectomy and other vascular procedures usually comprise an elongate core member with one or more tapered sections near the distal end thereof and a flexible body member such as a helical coil or a tubular body of polymeric material disposed about the distal portion of the core member. A shapable member, which may be the distal end of the core member or a separate shapeable ribbon which is secured to the distal end of the core member extends through the flexible body and is secured to the distal end of the flexible body by soldering, brazing or welding which forms a rounded distal tip. Torquing means are provided on the proximal end of the core member to rotate, and thereby steer, the guidewire while it is being advanced through a patient's vascular system. The leading tip is highly flexible and will not damage or perforate the vessel and the portion behind the distal tip is increasingly stiff which better supports a balloon catheter or similar device.

Currently available guidewires for use in peripheral vasculature do not have a sufficiently soft and flexible distal tip with radiopaque characteristics. They have poor torque response due to helical coil members covering the entire length of the device. Also, physicians using the currently available guidewires of larger outer diameter have difficulty identifying which portion of the guidewire is adjacent the desired location within the vasculature. That is, because the distal sections of guidewires typically have a tapered core wire therein, the diameter of which in part determines the flexibility of the section, it is desirable for the physician to be able to easily determine the relative amount of support the guidewire will offer at a given location via fluoroscopic imaging.

What has been needed is a relatively large outer diameter guidewire for use in the peripheral vasculature and carotid arteries that has a high degree of torsional control, a soft and flexible distal tip with radiopaque signature, and a stable outer coil configuration. Also, it is desirable to have outer coils which are visible under fluoroscopy, but which do not require the use of precious metal components. In addition, it is desirable to have fluoroscopic markers to indicate the core wire taper transitions so that the physician may easily determine whether the diagnostic or therapeutic device is over a flexible portion or more rigid and supportive portion of the guidewire. The present invention satisfies these and other needs.

SUMMARY

The present invention is directed to a guidewire having an elongate core member with a proximal section and a distal section. The distal section has at least one tapered segment, wherein the elongate core member tapers distally to a reduced diameter, thereby increasing the flexibility of the core member in a distal direction. Preferably, the tapered segments of the distal section of the elongate core member are marked with radiopaque markers to indicate where a tapered segment begins or ends. In this way, a physician using the guidewire is able to identify the relative flexibility and stiffness of an area of interest on the guidewire using fluoroscopic imaging.

A proximal coil, which has a proximal end and a distal end, is disposed around at least a portion of the distal section of the elongate core member. The proximal coil is a helix of material which has a substantially rectangular cross section. The rectangular cross section provides increased stiffness and coil integrity as compared to material with a round cross section of similar thickness, due to the increased cross sectional area. The proximal end of the proximal coil is attached to the distal section of the elongate core member.

A distal coil having a distal end and a proximal end is also disposed at least partially around the distal section of the elongate core member, distally of the proximal coil. The distal coil is also a helix, but is made of material that is substantially round in cross section, and preferably, is radiopaque. The distal coil may be entirely radiopaque, or it may be made of segments of radiopaque and non-radiopaque material. The radiopaque and non-radiopaque segments can be used to indicate the location of the beginning or end of a tapered segment of the elongate core member in place of or in conjunction with the radiopaque markers attached to the elongate core member discussed above. The round cross section of the material from which the distal coil is made gives the distal coil greater flexibility, which is desirable for the distal end of the guidewire.

The distal coil or segments thereof can be made of a homogeneous material that is radiopaque, but may also be made of a non-radiopaque hollow tube that is filled with material that is at least partially radiopaque. In this way, the hollow tube material can be chosen for its mechanical properties that enhance the guidewire's performance, and the radiopaque filler material can be chosen for its cost effectiveness or other desirable attributes. The proximal end of the distal coil is attached to the distal end of the proximal coil, and the distal end of the distal coil is attached to the distal section of the elongate core member. These and other advantages of the invention will become more apparent from the following detailed description of the invention when taken in conjunction with the accompanying exemplary drawings.

BRIEF DESCRIPTION OF THE DRAWINGS

FIG. 4 is a transverse cross sectional view of the preferred embodiment of FIG. 1 taken at 4—4.

FIG. 5 is a transverse cross sectional view of the preferred embodiment of FIG. 1 taken at 5—5.

FIG. 6A is a transverse cross sectional view of the preferred embodiment of FIG. 1 taken at 6—6.

FIG. 6B is a transverse cross sectional view of an alternative preferred embodiment of the invention as shown in FIG. 1 taken at 6—6.

DETAILED DESCRIPTION OF THE INVENTION

Figure 1:
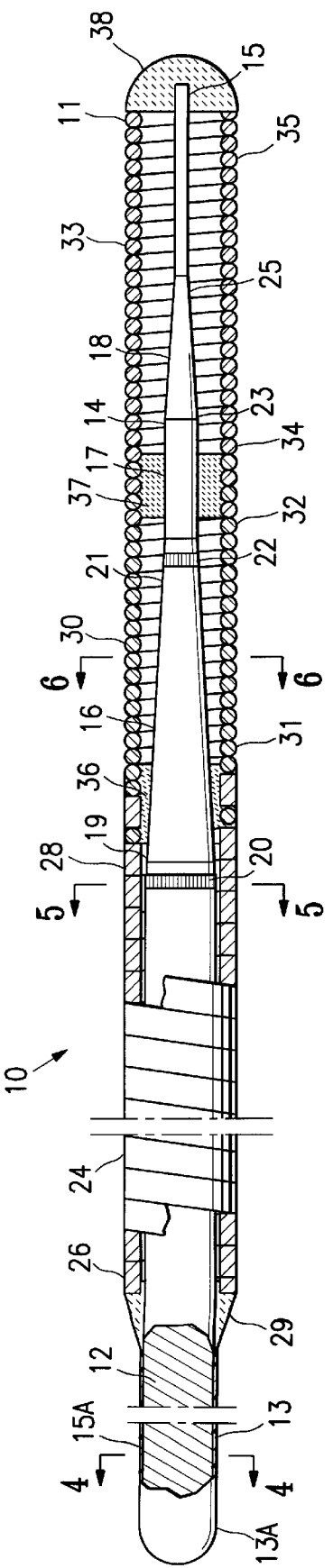
FIG. 1 depicts an elevational view of a preferred embodiment of the invention in partial section.

In FIG. 1, a guidewire 10 with a distal tip 11 is shown which has features of the present invention. The guidewire 10 can be from about 43 inches (110 cm) to about 140 inches (355 cm) in overall length, but is preferably about 55 inches (140 cm) to about 122 inches (310 cm) in length. In addition, the guidewire 10 has specific preferred embodiments having overall lengths of about 57 inches (145 cm), about 75 inches (190 cm), and about 118 inches (300 cm).

The guidewire 10 has an elongate core member 12 with a proximal section 13 and a distal section 14. The proximal section terminates proximally in a proximal end 13A, and the distal end terminates distally in a distal end 15. The distal end 15 preferably has a substantially round cross section, but may be flattened in order to facilitate shaping of the distal tip of the guidewire 11 by the user. The proximal section 13 of the elongate core member can have an outer diameter of about 0.017 inches (0.4 mm) to about 0.030 inches (0.8 mm), but preferably has an outer diameter of about 0.020 inches (0.5 mm) to about 0.027 inches (0.7 mm). The elongate core member 12 may be formed of stainless steel, specifically 304V stainless steel, NiTi alloys or combinations thereof such as described in U.S. Pat. No. 5,341,818 (Abrams et al) which has been incorporated by reference. Other materials may also be used such as high strength alloys described in U.S. patent application Ser. No. 08/829,465 (Fariabi), filed Mar. 28, 1997, entitled HIGH STRENGTH MEMBER FOR INTRACORPOREAL USE which is incorporated herein by reference in its entirety. The elongate core member 12 may be coated, at least in part, with a lubricious coating 15A such as a fluoropolymer, e.g. TEFLON® available from DuPont. Another coating that may be used is or MICROGLIDE™ coating, used by the present assignee, Advanced Cardiovascular Systems, Inc. on many of its commercially available guidewires. Hydrophyillic coatings may also be used.

The distal section 14 has a first tapered segment 16 and a second tapered segment 18, wherein the elongate core member 12 tapers distally to a reduced diameter, thereby increasing the flexibility of the core member in a distal direction. The first tapered segment 16 of the distal section 14 of the elongate core member has a proximal end 19 which is marked with a proximal marker 20, and a distal end 21 which is marked with a distal marker 22. The proximal marker 20 and distal marker 22 are radiopaque markers that indicate the location of the proximal end 19 and distal end 21 of the first tapered segment under fluoroscopy. The proximal marker 20 and distal marker 22 are preferably made of a radiopaque metal such as gold or tantalum, but may be made of any suitable radiopaque material, such as bismuth or barium. The proximal marker 20 and distal marker 22 are preferably attached to the distal end of the elongate core member 12 by soldering, brazing, bonding with an adhesive such as epoxy or cyanoacrylate, or by mechanically crimping in place.

The proximal marker 20 and distal marker 22 have a cross section with a thickness of about 0.0005 inches (0.013 mm) to about 0.004 inches (0.1 mm), preferably about 0.001 inches (0.025 mm) to about 0.002 inches (0.05 mm). The proximal marker 20 and the distal marker 22 can have a width of about 0.010 inches (0.25 mm) to about 0.10 inches (2.5 mm), preferably about 0.030 inches (0.76 mm) to about 0.070 inches (1.8 mm), and more preferably about 0.050 inches (1.3 mm).

The outer diameter of the proximal end 19 of the first tapered segment can be from about 0.017 inches (0.4 mm) to about 0.030 inches (0.8 mm), but is preferably about 0.020 inches (0.5 mm) to about 0.027 inches (0.7 mm). The distal end 21 of the first tapered segment can have an outer diameter of about 0.008 inches ((0.2 mm) to about 0.014 inches (0.36 mm), but is preferably about 0.009 inches (0.23 mm) to about 0.013 inches (0.33 mm), and more preferably about 0.010 inches (0.25 mm) to about 0.012 inches (0.3 mm). The length of the first tapered segment 16 can be from about 2 inches (5 cm) to about 3.5 inches (9 cm), but is preferably from about 2.4 inches (6 cm ) to about 3.1 inches (8 cm).

The second tapered segment 18 has a proximal end 23 and a distal end 25. The outer diameter of the proximal end 23 of the second tapered segment can be from about 0.008 inches (0.2 mm) to about 0.014 inches (0.36 mm), but is preferably about 0.009 inches (0.23 mm) to about 0.013 inches (0.33 mm), and more preferably about 0.010 inches (0.25 mm) to about 0.012 inches (0.3 mm). The outer diameter of the distal end 25 of the second tapered segment 18 can be from about 0.002 inches (0.05 mm) to about 0.006 inches (0.15 mm), preferably about 0.003 inches (0.08 mm) to about 0.005 inches (0.13 mm), more preferably about 0.004 inches (0.1 mm). The length of the second tapered segment 18 can be from about 0.4 inches (1 cm) to about 2 inches (5 cm), preferably about 0.8 inches (2 cm) to about 1.6 inches (4 cm), and more preferably about 1.38 inches (3.5 cm).

The first tapered segment 16 and second tapered segment 18 can be adjacent, but preferably are separated by a constant diameter segment 17 which is disposed between the first tapered segment and the second tapered segment. The outer diameter of the constant diameter segment 17 can be about 0.008 inches (0.2 mm) to about 0.014 inches (0.36 mm), but is preferably about 0.009 inches (0.23 mm) to about 0.013 inches (0.33 mm), and more preferably about 0.010 inches (0.25 mm) to about 0.012 inches (0.3 mm).

Figure 3:
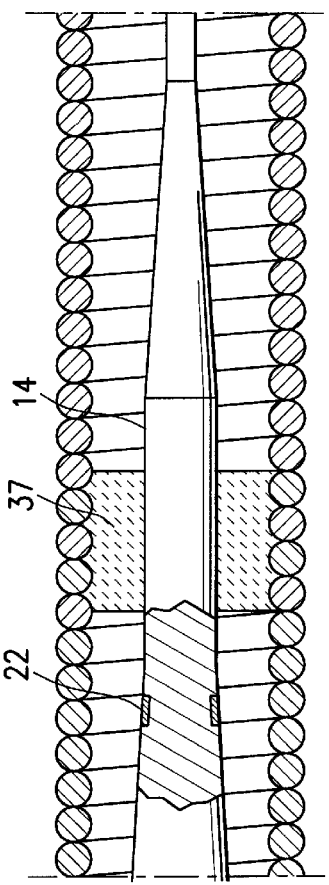
FIG. 3 is a magnified view of the preferred embodiment of FIG. 1 taken in an area between the first tapered segment and second tapered segment.
Figure 2:
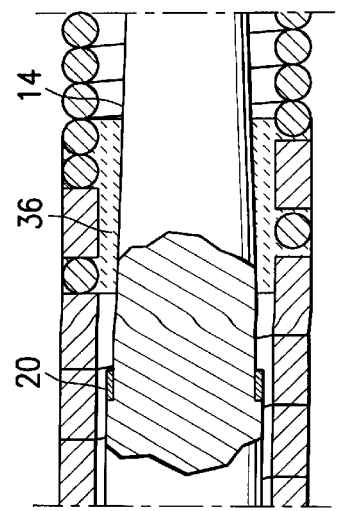
FIG. 2 shows a magnified view of the preferred embodiment of FIG. 1 taken in area of section 5—5.

FIG. 2 shows the proximal marker 20 in a cross sectional view and illustrates the placement of the proximal marker on the distal section of the elongate core member 14. FIG. 3 shows the distal marker 22 and its placement on the distal section of the elongate core member 14. The proximal marker 20 and distal marker 22 identify the relative flexibility and stiffness of an area of interest on the guidewire under fluoroscopic visualization. FIG. 4 shows a transverse cross sectional view of the proximal section of the elongate core member 13 and the lubricious coating 15A.

Referring again to FIG. 1, a proximal coil 24, which has a proximal end 26 and a distal end 28, is disposed around at least a portion of the distal section 14 of the elongate core member 12. The proximal coil 24 is a helix of material which has a substantially rectangular cross section. The rectangular cross section provides increased stiffness and coil integrity as compared to material with a round cross section for a similar thickness, due to the increased cross sectional area. The substantially rectangular cross section of the helix material of the proximal coil 24 can have a thickness of about 0.002 inches (0.05 mm) to about 0.006 inches (0.15 mm), preferably about 0.003 inches (0.08 mm) to about 0.005 inches (0.13 mm). The width of the rectangular cross section of the helix material can be about 0.006 inches (0.15 mm) to about 0.018 inches (0.46 mm), preferably about 0.010 inches (0.25 mm) to about 0.014 inches (0.36 mm), and more preferably about 0.011 inches (0.28 mm) to about 0.013 inches (0.33 mm).

The outer diameter of the proximal coil 24 can be about 0.018 inches (0.76 mm) to about 0.040 inches (1 mm), preferably about 0.03 inches (0.76 mm) to about 0.037 inches (0.94 mm). The length of the proximal coil can be from about 20 inches (50 cm) to about 55 inches (140 cm), preferably about 31.5 inches (80 cm) to about 45 inches (115 cm), and more preferably about 35 inches (90 cm) to about 39 inches (100 cm). The proximal end of the proximal coil 26 is attached to the distal section of the elongate core member 14 by a proximal solder 29.

FIG. 5 shows a transverse cross sectional view of the elongate core member 12 and the proximal coil 24 taken at section 5—5 of FIG. 1. The inner diameter of the proximal coil 24 is preferably spaced from the outer diameter of the elongate core member 12. The proximal coil 24 is preferably made of a biocompatible material such as stainless steel, specifically, 304V stainless steel, but may be made from any suitable material having appropriate mechanical properties such as Co—Ni—Cr—Mo alloys (e.g. MP35N) or NiTi alloy, which can have pseudoelastic or shape memory characteristics, or both in combination. The proximal coil 24 may be coated, at least in part, with a lubricious coating such as a fluoropolymer, e.g. TEFLON® available from DuPont, or MICROGLIDE™ coating used by the present assignee, Advanced Cardiovascular Systems, Inc. on many of its commercially available guidewires. Hydrophyillic coatings may also be used.

Referring again to FIG. 1, a first distal coil 30 having a proximal end 31 and a distal end 32 is disposed at least partially around the distal section of the elongate core member 14, distally of the proximal coil 24. A second distal coil 33 is disposed about the distal section of the elongate core member 14 distally of the first distal coil 30. The second distal coil 33 has a proximal end 34 and a distal end 35. The proximal end 31 of the first distal coil 30 is attached to the distal end 28 of the proximal coil 24 by a butt solder 36. The distal end 32 of the first distal coil 30 is attached to the proximal end 34 of the second distal coil 33 by an intermediate solder 37. The distal end of the second distal coil 35 is preferably attached to the distal section of the elongate core member 14 by a distal solder 38. The first distal coil 30 is a helix and is made of material that is substantially round in cross section, and preferably, is radiopaque. The radiopaque image of the first distal coil can be used to delineate the extent of the first tapered section 16 of the distal section of elongate core member 14. The delineation of the first tapered segment 16 can be in addition to the delineation generated by the proximal marker 20 and distal marker 22, or in place of said markers.

The second distal coil 33 is also formed from a material that is round in cross section, but is preferably non-radiopaque. However, either or both of the distal coils 30 and 33 may be radiopaque, non-radiopaque, or may be combined into a single helical coil of material with a substantially round cross section. The round cross section of the material from which the distal coils 30 and 33 are made gives the distal coil greater flexibility, which is desirable for the distal end of the guidewire 11. The diameter of the helix material of the distal coils 30 and 33 can be about 0.003 inches (0.08 mm) to about 0.010 inches (0.25 mm), preferably about 0.004 inches (0.1 mm) to about 0.007 inches (0.18 mm) and more preferably, about 0.005 inches (0.13 mm) to about 0.006 inches (0.15 mm). The outer diameter of the distal coils 30 and 33 can be about 0.018 inches (0.8 mm) to about 0.040 inches (1 mm), preferably about 0.033 inches (0.8 mm) to about 0.037 inches (0.9 mm).

A transverse cross sectional view of the distal section of the elongate core member 14 and the first distal coil 30 is shown in FIG. 6A. The distal coils 30 and 33 are preferably made of a radiopaque metal such as tantalum, gold, platinum or alloys thereof. However, any suitable alloy or material can be used, such as 304V stainless steel, and various high strength, shape memory or pseudoelastic alloys as previously described (e.g., NiTi and MP35N) and may also be coated with a radiopaque material. The distal coils 30 and 33 may be coated, at least in part, with a lubricious coating such as a fluoropolymer, e.g. TEFLON®) available from DuPont, or MICROGLIDE™ coating used by the present assignee, Advanced Cardiovascular Systems, Inc. on many of its commercially available guidewires. Hydrophyillic coatings may also be used.

An alternative embodiment of the first distal coil 30 is shown in FIG. 6B, wherein the distal coil is made of a hollow tube 39 that is filled with a radiopaque filler 40 which is at least partially radiopaque. In this way, the hollow tube 39 that forms the first distal coil 30 can be made from a material that is chosen for its mechanical properties that enhance the performance of the guidewire 10, and the radiopaque filler 40 can be chosen for its safety and cost effectiveness or other desirable attributes. The hollow tube can have an outer diameter of about 0.003 inches to about 0.010 inches, preferably about 0.004 inches to about 0.007 inches and more preferably, about 0.005 inches to about 0.006 inches. The hollow tube 39 is preferably made of a material such as stainless steel, specifically, 304V stainless steel, but may be made from any suitable biocompatible material having the appropriate mechanical properties such as Co—Ni—Cr—Mo alloys (e.g. MP35N) or NiTi alloy, which can have pseudoelastic or shape memory characteristics, or both in combination. Other alloys that may be used have been described in U.S. patent application Ser. No. 08/829,465 (Fariabi), filed Mar. 28, 1997, entitled HIGH STRENGTH MEMBER FOR INTRACORPOREAL USE, which has been incorporated by reference herein. The radiopaque filler 40 is preferably made, at least in part, by tantalum powder. In addition to tantalum, other radiopaque powders or materials could be used, e.g. barium, bismuth, gold, platinum, or the like. Note that the alternative structure described above with regard to FIG. 6B could also be used for the structure of the second distal coil 33.

Figure 7:
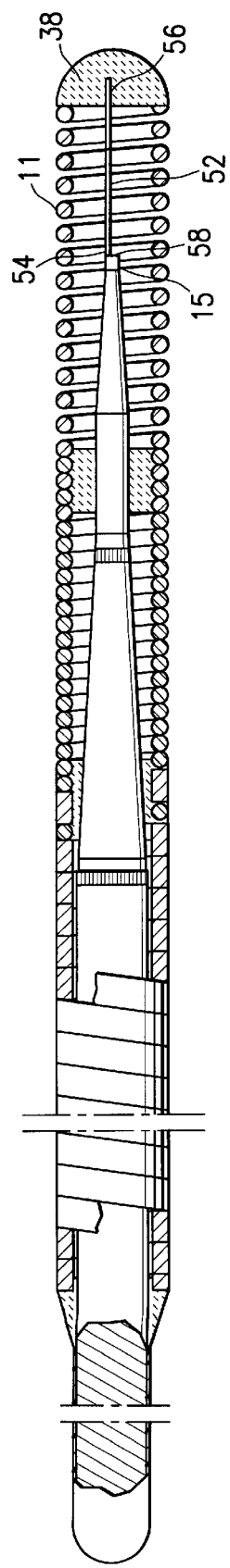
FIG. 7 is an elevational view of an alternative embodiment of the invention which includes a shaping ribbon at the distal end of the elongate core.

FIG. 7 shows an elevational view of an alternate embodiment of the invention wherein the distal tip of the guidewire 11 further comprises a shaping ribbon 52 similar to that described in U.S. Pat. No. 5,135,503 (Abrams) which has been incorporated by reference herein. The shaping ribbon 52 has a proximal end 54 and a distal end 56. The proximal end of the shaping ribbon 54 is preferably attached to the distal end of the elongate core member 15 by a shaping ribbon proximal solder 58. The proximal end of the shaping ribbon may also be attached to the distal end of the elongate core member by a variety of other methods, including, but not limited to, bonding by adhesives, and mechanical crimping. The distal end of the shaping ribbon 56 is attached to the distal end of the second distal coil 33 by the distal solder 38. The shaping ribbon 52 has a length of about 1 cm to about 7 cm, preferably about 3 cm to about 5 cm. The shaping ribbon is preferably flat-ended, but may also have a round cross section with an outer-diameter of about 0.002 inches to about 0.006 inches, preferably about 0.003 inches to about 0.005 inches, and more preferably about 0.004 inches. The shaping ribbon is preferably made of a biocompatible material such as stainless steel, specifically, 304V stainless steel, but may be made from any suitable material having the appropriate mechanical properties such as Co—Ni—Cr—Mo alloys (e.g. MP35N) or NiTi alloy, which can have pseudoelastic or shape memory characteristics, or both in combination.

While particular forms of invention have been illustrated and described, it will be apparent that various modifications can be made without departing from the spirit and scope of the invention. Accordingly, it is not intended that the invention be limited, except as by the appended claims.

What is claimed is:

1. A guidewire comprising:
   a) an elongate core member which has a proximal section with a substantially constant outer diameter, and a distal section having a distally tapered segment with a distal end and a proximal end marked with a radiopaque marker disposed on the elongate core member;
   b) a proximal coil which has a proximal end and a distal end, and which is at least partially disposed about the distal section of the elongate core member, which is comprised of a helix of ribbon material having a substantially rectangular cross section, and which has the proximal end secured to the proximal section of the elongate core member; and
   c) a distal coil which has a proximal end and a distal end, which is at least partially disposed about the distal section of the elongate core member distally of the proximal coil, and which is comprised of a helix of material having a substantially round cross section, and which has its distal end secured to the elongate core member.

2. The guidewire of claim 1 wherein the distal end of the elongate core member is flattened.

3. The guidewire of claim 1 wherein the distal end of the distally tapered segment is marked by a radiopaque marker disposed on the elongate core member.

4. The guidewire of claim 1 further comprising a lubricious coating disposed on the elongate core member proximal to the proximal end of the proximal coil.

5. The guidewire of claim 4 wherein the lubricious coating is comprised of a lubricious polymer.

6. The guidewire of claim 1 wherein the distal end of the distal coil is attached to the distal end of the elongate core member with a gold ball solder.

7. The guidewire of claim 1 wherein the distal coil is at least partially radiopaque.

8. The guidewire of claim 7 wherein the distal coil is comprised of drawn filled tubing, filled at least partially with a radiopaque material.

9. The guidewire of claim 8 wherein the radiopaque material is tantalum.

10. The guidewire of claim 1 wherein the proximal coil and the distal coil have an outer surface and an inner surface, and have at least the outer surface coated with a lubricious coating.

11. The guidewire of claim 10 wherein the lubricious coating is comprised of a fluoropolymer material.

12. The guidewire of claim 1 wherein the distal coil is about 10 cm to about 24 cm in length.

13. The guidewire of claim 1 wherein the proximal coil is about 90 cm to about 100 cm in length.

14. The guidewire of claim 1 wherein the proximal section of the elongate core member is about 0.018 inches to about 0.027 inches in diameter.

15. The guidewire of claim 1 wherein the proximal coil is about 0.018 inches to about 0.037 inches in outer diameter and the distal coil is about 0.018 inches to about 0.037 inches in outer diameter.

16. The guidewire of claim 1 wherein the distal section of the elongate core member terminates distally in a distal end, and further comprising a shaping ribbon having a proximal end and a distal end with the proximal end of the shaping ribbon secured to the distal end of the distal section of the elongate core member.

17. The guidewire of claim 16 wherein the distal end of the distal coil is secured to the shaping ribbon.

18. A guidewire comprising:
   a) an elongate core member which has a proximal section with a substantially constant outer diameter, and a distal section having a distally tapered segment;
   b) a proximal coil which has a proximal end and a distal end, and which is at least partially disposed about the distal section of the elongate core member, which is comprised of a helix of non-radiopaque ribbon material having a substantially rectangular cross section, and which has the proximal end secured to the proximal section of the elongate core member;
   c) a first distal coil which has a proximal end and a distal end, which is at least partially disposed about the distal section of the elongate core member distally adjacent the proximal coil, which is comprised of a helix of radiopaque material having a substantially round cross section, and which is axially coextensive with the distally tapered segment; and
   d) a second distal coil which has a proximal end and a distal end, which is at least partially disposed about the distal section of the elongate core member distally adjacent the first distal coil, and which is comprised of a helix of non-radiopaque material having a substantially round cross section.

19. The guidewire of claim 18 wherein the first distal coil is comprised of a drawn filled tubing.

20. The guidewire of claim 18 wherein the distal section of the elongate core member terminates distally in a distal end, and further comprising a shaping ribbon having a proximal end and a distal end with the proximal end of the shaping ribbon secured to the distal end of the distal section of the elongate core member.

21. The guidewire of claim 20 wherein the distal end of the second distal coil is secured to the shaping ribbon.

\* \* \* \* \*